(12) United States Patent
Choi et al.

(10) Patent No.: US 10,300,472 B2
(45) Date of Patent: May 28, 2019

(54) CATALYST COMPOSITION CONTAINING PHOSPHOROUS-BASED LIGAND AND METHOD FOR HYDROFORMYLATION USING SAME

(71) Applicant: LG CHEM, LTD., Seoul (KR)

(72) Inventors: Min Ji Choi, Daejeon (KR); Mi Young Kim, Daejeon (KR); Sung Shik Eom, Daejeon (KR); Dong Hyun Ko, Daejeon (KR); Da Won Jung, Daejeon (KR); Tae Yun Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/535,659

(22) PCT Filed: Oct. 4, 2016

(86) PCT No.: PCT/KR2016/011067
§ 371 (c)(1),
(2) Date: Jun. 14, 2017

(87) PCT Pub. No.: WO2017/061745
PCT Pub. Date: Apr. 13, 2017

(65) Prior Publication Data
US 2018/0272326 A1    Sep. 27, 2018

(30) Foreign Application Priority Data

Oct. 5, 2015 (KR) ........................ 10-2015-0139571

(51) Int. Cl.
| | | |
|---|---|---|
| *C07C 45/50* | (2006.01) | |
| *B01J 31/00* | (2006.01) | |
| *B01J 31/24* | (2006.01) | |
| *B01J 31/28* | (2006.01) | |

(52) U.S. Cl.
CPC ........... *B01J 31/2404* (2013.01); *B01J 31/24* (2013.01); *B01J 31/28* (2013.01); *C07C 45/50* (2013.01); *B01J 2231/321* (2013.01); *B01J 2531/821* (2013.01); *B01J 2531/822* (2013.01); *B01J 2531/824* (2013.01); *B01J 2531/825* (2013.01); *B01J 2531/827* (2013.01); *B01J 2531/828* (2013.01); *B01J 2531/842* (2013.01); *B01J 2531/845* (2013.01); *B01J 2531/847* (2013.01)

(58) Field of Classification Search
CPC .... C07C 45/50; C07C 45/505; B01J 31/2404; B01J 2531/822
See application file for complete search history.

(56) References Cited

U.S. PATENT DOCUMENTS

| | | | |
|---|---|---|---|
| 6,153,800 A | 11/2000 | Gelling et al. | |
| 8,178,729 B2* | 5/2012 | Karvinen | B01J 31/2404 568/451 |
| 2008/0281128 A1 | 11/2008 | Karvinen et al. | |

FOREIGN PATENT DOCUMENTS

| | | |
|---|---|---|
| KR | 10-2007-0116109 A | 12/2007 |
| KR | 10-2010-0092399 A | 8/2010 |
| KR | 10-1095775 B1 | 12/2011 |
| KR | 10-2013-0131516 A | 12/2013 |
| KR | 10-2015-0015904 A | 2/2015 |

* cited by examiner

*Primary Examiner* — Sikarl A Witherspoon
(74) *Attorney, Agent, or Firm* — Dentons US LLP

(57) ABSTRACT

The present invention relates to a catalyst composition including a phosphorous-based ligand, and a hydroformylation method using the catalyst composition. More particularly, the present invention relates to a catalyst composition, which includes two different kinds of monocoordinated phosphine ligands and a transition metal catalyst, and a hydroformylation method using the catalyst composition. In accordance with the present invention, a catalyst composition lowering a selection ratio of normal aldehyde to iso aldehyde (n/i ratio), which are generated during hydroformylation of an olefinic compound, and exhibiting superior catalytic activity and stability, and a method of hydroformylating an olefinic compound using the catalyst composition are provided.

14 Claims, 1 Drawing Sheet

CATALYST COMPOSITION CONTAINING PHOSPHOROUS-BASED LIGAND AND METHOD FOR HYDROFORMYLATION USING SAME

CROSS-REFERENCE TO RELATED APPLICATION(S)

This application Is a National Stage Application of International Application No. PCT/KR2016/011067 filed on Oct. 4, 2016, which claims the benefit of Korean Patent Application No. 10-2015-0139571, filed on Oct. 5, 2015, all of which are hereby incorporated by reference in their entirety for all purposes as if fully set forth herein.

TECHNICAL FIELD

The present invention relates to a catalyst composition including a phosphorous-based ligand and a hydroformylation method using the catalyst composition. More particularly, the present invention relates to a catalyst composition that lowers a selection ratio of normal aldehyde to iso aldehyde (n/i ratio), which are generated during hydroformylation of an olefinic compound, and exhibits superior catalytic activity and stability and a method of hydroformylating an olefinic compound using the catalyst composition.

BACKGROUND ART

Hydroformylation, for production of linear (normal) and branched (iso) aldehydes, a carbon number of each of which is increased by one, by reacting various olefins with carbon monoxide (CO) and hydrogen ($H_2$), which are generally referred to as synthesis gases, in the presence of a homogeneous organometallic catalyst and a ligand, was first discovered by Otto Roelen in Germany in 1938.

Hydroformylation, which is also known as oxo synthesis, is very important in industrial homogeneous catalytic reaction. Throughout the world, various aldehydes including alcohol derivatives are produced and consumed through the oxo process.

Various aldehydes, which are synthesized by oxo reaction, may be modified into various acids and alcohols with a long alkyl group by performing oxidization and hydrogenation after performing condensation reaction with aldol or the like. In particular, a hydrogenated alcohol, which is derived from an aldehyde synthesized by such oxo synthesis, is called an oxo alcohol. Such an oxo alcohol is widely utilized industrially as a raw material of solvents, additives, various plasticizers, synthetic lubricating oils, and the like.

Conventionally, the value of linear (normal) aldehyde derivatives among aldehydes generated by oxo synthesis was high, whereby most research on catalysts has focused on increasing the proportion of linear aldehyde derivatives. However, in recent years, isobutyric acid, neopentyl glycol (NPG), 2,2,4-trimethyl-1,3-pentanediol, isovaleric acid and the like, which use a branched aldehyde derivative (iso-aldehyde) as a raw material, were developed, and thus, demand for iso-aldehydes has increased. Accordingly, research has been carried out to increase selectivity for the branched aldehyde derivative. Therefore, there is an urgent need for a catalyst exhibiting superior catalyst stability and activity while lowering a selection ratio of normal aldehyde to iso aldehyde (n/i ratio).

RELATED ART DOCUMENT

[Patent Document] (Patent Document 1) KR 2010-0092399 A

DISCLOSURE

Technical Problem

Therefore, the present invention has been made in view of the above problems, and it is one object of the present invention to provide a catalyst composition that lowers a selection ratio of normal aldehyde to iso aldehyde (n/i ratio), which are generated during hydroformylation of an olefinic compound, and exhibits superior catalytic activity and stability.

It is another object of the present invention to provide a method of hydroformylating an olefinic compound using the catalyst composition.

The above and other objects can be accomplished by the present disclosure described below.

Technical Solution

In accordance with an aspect of the present invention, the above and other objects can be accomplished by the provision of a catalyst composition including a monocoordinated phosphine ligand represented by Formula 1 below; a monocoordinated phosphine ligand represented by Formula 2 below; and a transition metal catalyst represented by Formula 3 below:

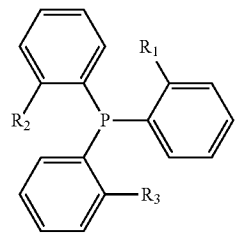

[Formula 1]

wherein $R_1$, $R_2$ and $R_3$ are each independently a $C_1$ or $C_2$ alkyl group or a $C_1$ or $C_2$ alkoxy group,

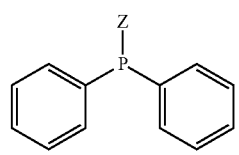

[Formula 2]

wherein Z is a $C_5$ to $C_{10}$ cycloalkyl group, and

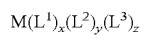

$M(L^1)_x(L^2)_y(L^3)_z$ [Formula 3]

wherein M is one selected from the group consisting of cobalt (Co), rhodium (Rh), iridium (Ir), ruthenium (Ru), iron (Fe), nickel (Ni), palladium (Pd), platinum (Pt) and osmium (Os), $L^1$, $L^2$ and $L^3$ are each independently one selected from the group consisting of hydrogen, carbonyl (CO), cyclooctadiene, norbornene, chlorine, triphenylphosphine (TPP), and acetylacetonato (AcAc), and x, y and z are each independently 0 to 5, but x, y and z are not simultaneously 0.

In accordance with another aspect of the present invention, there is provided a method of hydroformylating an olefinic compound, the method including a step of preparing an aldehyde by reacting an olefinic compound with a synthetic gas of carbon monoxide and hydrogen ($CO/H_2$) in the presence of the catalyst composition.

Advantageous Effects

As apparent from the above description, the present invention provides a catalyst composition that lowers a selection ratio of normal aldehyde to iso aldehyde (n/i ratio), which are generated during hydroformylation of an olefinic compound, and exhibits superior catalytic activity and stability.

In addition, the present invention provides a method of hydroformylating an olefinic compound using the catalyst composition.

BEST MODE

Figure 1:
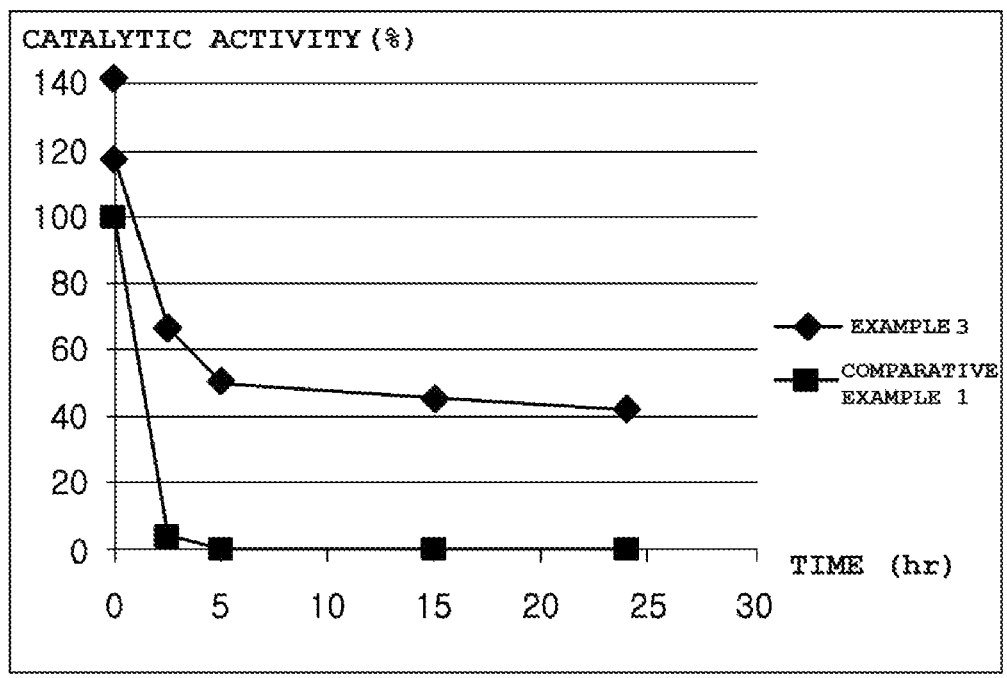
FIG. 1 illustrates a comparative graph of catalytic activity and stability of a catalyst composition prepared according to each of Example 3 and Comparative Example 1 of the present invention.

Hereinafter, the present invention is described in detail.

The present inventors confirmed that, when two different kinds of monocoordinated phosphine ligands, which respectively have specific structures, are simultaneously applied to a catalyst composition used for hydroformylation of an olefin, superior catalytic activity and stability are exhibited while lowering a selection ratio of normal aldehyde to iso aldehyde (n/i ratio), compared to a catalyst composition to which a conventional phosphine ligand is applied, thus completing the present invention.

The catalyst composition according to the present invention is characterized by including two different kinds of monocoordinated phosphine ligands and a transition metal catalyst.

Constituents of the catalyst composition are now described in detail.

The two different monocoordinated phosphine ligands may be respectively represented by, for example, Formulas 1 and 2 below:

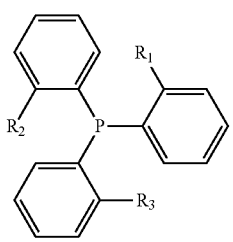

[Formula 1]

wherein $R_1$, $R_2$ and $R_3$ may be each independently a $C_1$ or $C_2$ alkyl group or a $C_1$ or $C_2$ alkoxy group. In another embodiment, $R_1$, $R_2$ and $R_3$ may be each independently a methyl group or a methoxy group.

In a specific embodiment, the monocoordinated phosphine ligand represented by Formula 1 may be tri-o-tolylphosphine or tris(o-methoxyphenyl)phosphine. In this case, a selection ratio of normal aldehyde to iso aldehyde (n/i ratio) may be lowered.

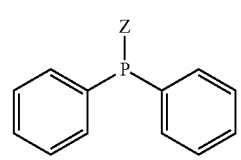

[Formula 2]

wherein Z may be a $C_5$ to $C_{10}$, $C_5$ to $C_8$, or $C_5$ to $C_7$ cycloalkyl group.

In a specific embodiment, the monocoordinated phosphine ligand represented by Formula 2 may be cyclopentyldiphenylphosphine or cyclohexyldiphenylphosphine. In this case, superior catalytic activity and stability are exhibited.

The content of each of the monocoordinated phosphine ligands represented by Formulas 1 and 2 may be, for example, 0.1 to 5% by weight, 0.1 to 3% by weight, or 0.5 to 3% by weight with respect to the catalyst composition. Within this range, superior catalytic activity and stability are exhibited and a selection ratio of normal aldehyde to iso aldehyde (n/i ratio) is lowered.

A total of the monocoordinated phosphine ligands represented by Formulas 1 and 2 may be included in an amount of, for example, 0.2 to 10% by weight, 1 to 8% by weight, or 2 to 5% by weight with respect to the catalyst composition. Within this range, superior catalytic activity and stability are exhibited and a selection ratio of normal aldehyde to iso aldehyde (n/i ratio) is lowered.

A mix ratio by weight of the monocoordinated phosphine ligand represented by Formula 1 the monocoordinated phosphine ligand represented by Formula 2 may be, for example, 10:1 to 1:5, 5:1 to 1:3, or 5:1 to 1:2. Within this range, a selection ratio of normal aldehyde to iso aldehyde (n/i ratio) is lowered.

Each of the monocoordinated phosphine ligands represented by Formulas 1 and 2 may be included in an amount of, for example, 0.5 to 80 moles, 1 to 60 moles, or 1 to 40 moles based on 1 mole of a transition metal in the transition metal catalyst. Within this range, superior catalytic activity and stability are exhibited.

The transition metal catalyst may be, for example, a catalyst represented by Formula 3 below:

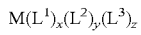

$$M(L^1)_x(L^2)_y(L^3)_z$$ [Formula 3]

wherein M may be, for example, one selected from the group consisting of cobalt (Co), rhodium (Rh), iridium (Ir), ruthenium (Ru), iron (Fe), nickel (Ni), palladium (Pd), platinum (Pt), and osmium (Os), $L^1$, $L^2$ and $L^3$ may be each independently, for example, one selected from the group consisting of hydrogen, carbonyl (CO), cyclooctadiene, norbornene, chlorine, triphenylphosphine (TPP), and acetylacetonato (AcAc), and x, y and z may be each independently, for example, 0 to 5, with the provision that x, y and z are not simultaneously 0.

In a specific embodiment, the transition metal catalyst may be one or more selected from the group consisting of cobalt carbonyl [$Co_2(CO)_8$], acetylacetonato dicarbonyl rhodium [Rh(AcAc)(CO)$_2$], rhodium acetylacetonato carbonyl triphenylphosphine [Rh(AcAc)(CO)(TPP)], hydrido carbonyl tri(triphenylphosphine)rhodium [HRh(CO)(TPP)$_3$], acetylacetonato dicarbonyl iridium [Ir(AcAc)(CO)$_2$], and hydrido carbonyl tri(triphenylphosphine)iridium [HIr(CO)(TPP)$_3$]. In this case, superior catalytic activity is exhibited.

The transition metal catalyst may be included, for example, in a content of 1 to 1,000 ppm, 10 to 800 ppm, or 50 to 500 ppm based on the catalyst composition. Within this range, a hydroformylation rate is excellent.

The catalyst composition may further include, for example, one or more solvents selected from the group consisting of propane aldehyde, butyraldehyde, pentyl aldehyde, valeraldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride, and heptane. In this case, superior catalytic activity is exhibited.

A method of hydroformylating the olefinic compound according to the present invention is not specifically limited so long as the method is a general hydroformylation method. In a specific embodiment, the method may include a step of preparing an aldehyde by reacting an olefinic compound with a synthetic gas of carbon monoxide and hydrogen (CO/H$_2$) in the presence of the catalyst composition.

The olefinic compound may be, for example, a compound represented by Formula 4 below:

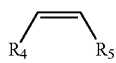

[Formula 4]

wherein R$_4$ and R$_5$ may be each independently hydrogen, a C$_1$ to C$_{20}$ alkyl group, fluorine (—F), chlorine (—Cl), bromine (—Br), trifluoromethyl (—CF$_3$), or a C$_6$ to C$_{20}$ aryl group substituted with 0 to 5 substituents, and the aryl group may be substituted with nitro (—NO$_2$), fluorine (—F), chlorine (—Cl), bromine (—Br), methyl, ethyl, propyl, or butyl.

In a specific embodiment, the olefinic compound may be one or more selected from the group consisting of ethene, propene, 1-butene, 1-pentene, 1-hexene, 1-octene and styrene.

A mix ratio in moles of carbon monoxide:hydrogen in the synthetic gas (CO/H$_2$) may be, for example, 5:95 to 70:30, 40:60 to 60:40, or 45:55 to 55:45. Within this range, the gases in the reaction are not accumulated, whereby the catalyst exhibits superior reactivity.

In the hydroformylation method, a reaction temperature of the olefinic compound and the synthetic gas (CO/H$_2$) in the presence of the catalyst composition may be 20 to 180° C., 50 to 150° C., or 75 to 125° C. Within this range, stability and activity of the catalyst are maintained during the hydroformylation.

In another embodiment, in the hydroformylation method, a reaction pressure of a reactor may be 1 to 700 bar, 1 to 300 bar, or 5 to 30 bar. Within this range, superior catalytic activity is exhibited.

The method of hydroformylating the olefinic compound may be represented by, for example, Reaction Formula 1 below:

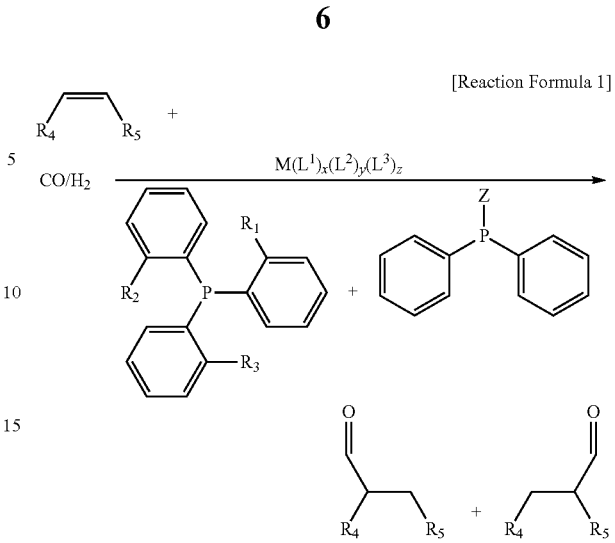

[Reaction Formula 1]

In a specific embodiment, the transition metal catalyst represented by Formula 3 and the two different monocoordinated phosphine ligands represented by Formulas 1 and 2 are dissolved in the solvent, thereby preparing a mixture solution of the transition metal catalyst and the ligands. The resultant mixture is fed along with the olefinic compound represented by Formula 4 and the synthetic gas (CO/H$_2$) into a general reactor, followed by elevating temperature and applying pressure while stirring such that hydroformylation occurs. As a result, an aldehyde may be produced.

An aldehyde prepared according to the method of hydroformylating an olefinic compound may have a selection ratio of normal aldehyde to iso aldehyde of, for example, 2.5 or less, 1.0 to 2.5, or 1.2 to 2.0.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

EXAMPLE

Examples 1 to 4 and Comparative Examples 1 to 8

0.122 g (0.3 mmol) of rhodium acetylacetonato carbonyl triphenylphosphine (Rh(AcAc)(CO)(TPP), ROPAC), as a catalyst, and ligands (L1 and L2) were dissolved in a valeraldehyde solvent such as a total amount of a resultant solution reached 100 g (Rh 250 ppm). Here, the amounts of the used ligands (L1 and L2) are summarized in a unit of % by weight in Table 1 below. The resultant solution was fed into a 600 ml autoclave reactor. A mixed gas including propylene and a synthetic gas (CO/H$_2$) that were mixed in a mole ratio of 1:1:1 (propylene:CO:H$_2$) was injected into the reaction solution, and an interior pressure of the reactor was maintained at 8 bar. Reaction was carried out at 90° C. for one hour while stirring.

[Test Example]

A selection ratio of normal aldehyde to iso aldehyde (n/i ratio), catalytic activity, and stability of a catalyst composition prepared according to each of Example 1 to 4 and Comparative Example 1 to 8 were measured according to the following methods. Results are summarized in Table 1 below.

Measurement methods

Selection ratio of normal aldehyde to iso aldehyde (n/i ratio): Was represented by dividing the amount of generated nomal-butyraldehyde by the amount of iso-butyraldehyde. Here, the generation amount of each of the nomal-butyraldehyde and the iso-butyraldehyde was obtained by gas chromatography (GC) after reaction.

Catalytic activity (normal activity (fresh), %): Was calculated according to Mathematical Equation 1 below and represented as a percentage. Particularly, catalytic activity was calculated by, to 100% by weight of a total of normal and iso butyraldehydes generated by injecting a mixed gas including propylene and a synthetic gas ($CO/H_2$), which were mixed in a mole ratio of 1:1:1 (propylene:$CO$:$H_2$), into a reaction solution prepared according to Comparative Example 1 and by stirring a resultant mixture at 90° C. for one hour while maintaining an interior pressure of a reactor at 8 bar, comparing a total weight of normal and iso butyraldehydes generated by reacting a reaction solution of each of the examples and the comparative examples under the same conditions.

Catalytic activity (fresh)=Total weight of normal and iso butyraldehydes of example or comparative example/total weight of normal and iso butyraldehydes of Comparative Example 1×100    [Mathematical Equation 1]

Catalytic stability (normal stability (aging), %): Was calculated according to Mathematical Equation 2 below to represent change in catalytic activity as a percentage. Particularly, a synthetic gas including CO and $H_2$ mixed in a mole ratio of 1:1 was injected into a reaction solution of each of examples and comparative examples and stirring was performed at 120° C. for 15 hours. Subsequently, a mixed gas including propylene and synthetic gas ($CO/H_2$) mixed in a mole ratio of 1:1:1 (propylene:$CO$:$H_2$) was injected into the resultant mixture, and stirring was performed at 90° C. for one hour while maintaining an interior pressure of a reactor at 8 bar such that reaction occurred. Subsequently, catalytic activity was measured. The measured catalytic activity was compared to that of Comparative Example 1 (fresh).

Catalytic stability (aging)=Total weight of normal and iso butyraldehydes of example or comparative example after 15 hours/total weight of 1.5 ormal and iso butyraldehydes of Comparative Example 1 (fresh)×100    [Mathematical Equation 2]

TABLE 1

| Classification | Catalyst (Rh) | L1 | L2 | L1 content | L2 content | n/i ratio | Catalytic activity (Fresh) | Catalytic stability (aging) |
|---|---|---|---|---|---|---|---|---|
| Example 1 | ROPAC | TOTP | CHDP | 3% by weight | 1% by weight | 1.80 | 199 | 52 |
| Example 2 | ROPAC | TOTP | CHDP | 2.5% by weight | 0.5% by weight | 1.70 | 250 | 40 |
| Example 3 | ROPAC | TOTP | CHDP | 2% by weight | 1% by weight | 1.83 | 117 | 45 |
| Example 4 | ROPAC | TOTP | CHDP | 1% by weight | 2% by weight | 1.95 | 101 | 32 |
| Comparative Example 1 | ROPAC | TOTP | — | 0.3% by weight | — | 1.5 | 100 | 0 |
| Comparative Example 2 | ROPAC | TOTP | — | 1% by weight | — | 1.6 | 125 | 0 |
| Comparative Example 3 | ROPAC | TOTP | — | 3% by weight | — | 1.6 | 152 | 0 |
| Comparative Example 4 | ROPAC | TOTP | — | 5% by weight | — | 1.6 | 304 | 0 |
| Comparative Example 5 | ROPAC | CHDP | — | 2% by weight | — | 2.0 | 106 | 37 |
| Comparative Example 6 | ROPAC | CHDP | — | 3% by weight | — | 2.1 | 72 | 39 |
| Comparative Example 7 | ROPAC | TOTP | TPP | 1% by weight | 5% by weight | 5.3 | — | — |
| Comparative Example 8 | ROPAC | CHDP | TPP | 1% by weight | 5% by weight | 7.0 | — | — |

TOTP: Tri-o-tolylphosphine
CHDP: Cyclohexyldiphenylphosphine
TPP: Triphenylphosphine As shown in Table 1, it can be confirmed that, in the cases of the catalyst compositions according to Examples 1 to 4 prepared according to the present invention, a selection ratio of normal aldehyde to iso aldehyde (n/i ratio) is maintained at 2.5 or less and superior catalytic activity and stability are exhibited (see FIGS. 1 and 2).

Figure 2:
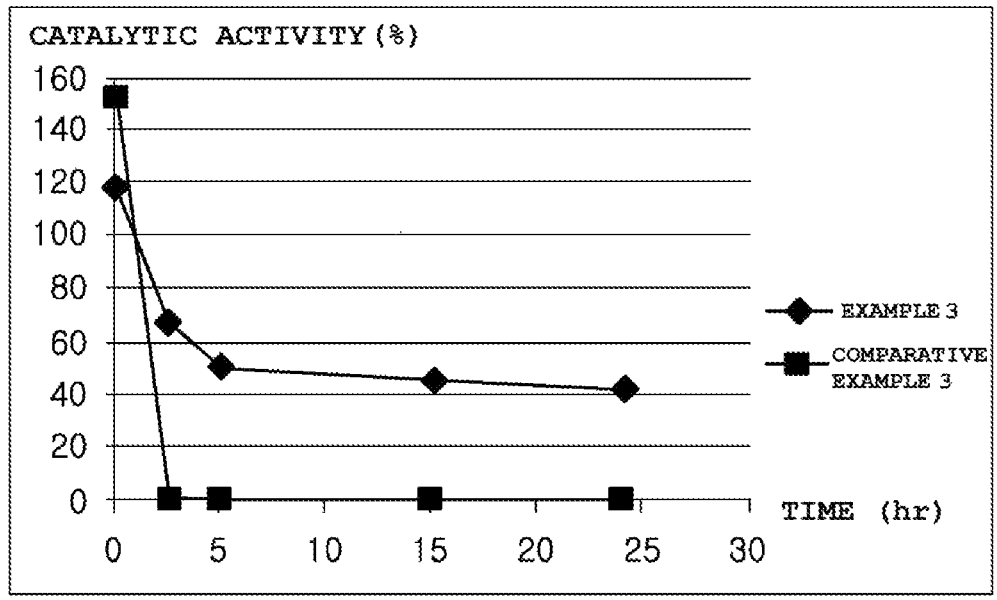
FIG. 2 illustrates a comparative graph of catalytic activity and stability of a catalyst composition prepared according to each of Example 3 and Comparative Example 3 of the present invention.

On the other hand, it can be confirmed that, in the cases of the catalyst compositions according to Comparative Examples 1 to 4 including only one ligand type, i.e., tri-o-tolylphosphine (TOTP), catalytic activity is rapidly decreased over time, and thus, catalytic stability is very poor (see FIGS. 1 and 2). In addition, it can be confirmed that, in the cases of the catalyst compositions according to Comparative Examples 5 and 6 including only one ligand type, i.e., cyclohexyldiphenylphosphine, a selection ratio of normal aldehyde to iso aldehyde (n/i ratio) is somewhat high and catalytic activity is rapidly decreased.

Further, it can be confirmed that, in the case of the catalyst composition according to Comparative Example 7 using tri-o-tolylphosphine (TOTP) and triphenylphosphine (TPP) together and the case of the catalyst composition according to Comparative Example 8 using cyclohexyldiphenylphosphine (CHDP) and triphenylphosphine (TPP) together, a selection ratio of normal aldehyde to iso aldehyde (n/i ratio) rapidly increases.

From these results, it can be confirmed that, when a transition metal catalyst is simultaneously applied with two different kinds of monocoordinated phosphine ligands respectively having specific structures according to the present invention, the expressive ligands may be used in an appropriate amount, which is preferable in terms of cost and commerciality. In addition, due to application of the catalyst composition of the present invention, a selection ratio of normal aldehyde to iso aldehyde (n/i ratio), which is generated during hydroformylation of an olefinic compound, may be remarkably lowered while maintaining the activity and stability of a catalyst.

The invention claimed is:

1. A catalyst composition, comprising a monocoordinated phosphine ligand represented by Formula 1 below; a monocoordinated phosphine ligand represented by Formula 2 below; and a transition metal catalyst represented by Formula 3 below:

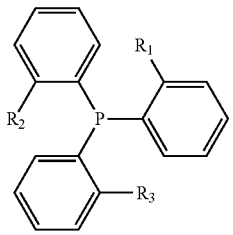

[Formula 1]

wherein $R_1$, $R_2$ and $R_3$ are each independently a $C_1$ or $C_2$ alkyl group or a $C_1$ or $C_2$ alkoxy group,

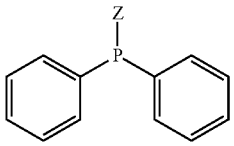

[Formula 2]

wherein Z is a $C_5$ to $C_{10}$ cycloalkyl group, and $$M(L^1)_x(L^2)_y(L^3)_z \quad \text{[Formula 3]}$$

wherein M is one selected from the group consisting of cobalt (Co), rhodium (Rh), iridium (Ir), ruthenium (Ru), iron (Fe), nickel (Ni), palladium (Pd), platinum (Pt) and osmium (Os), $L^1$, $L^2$ and $L^3$ are each independently one selected from the group consisting of hydrogen, carbonyl (CO), cyclooctadiene, norbornene, chlorine, triphenylphosphine (TPP), and acetylacetonato (AcAc), and x, y and z are each independently 0 to 5, but x, y and z are not simultaneously 0.

2. The catalyst composition according to claim 1, wherein each of the monocoordinated phosphine ligand represented by Formula 1 and the monocoordinated phosphine ligand represented by Formula 2 is comprised in a content of 0.1 to 5% by weight with respect to the catalyst composition.

3. The catalyst composition according to claim 1, wherein a mix ratio by weight of the monocoordinated phosphine ligand represented by Formula 1:the monocoordinated phosphine ligand represented by Formula 2 is 10:1 to 1:5.

4. The catalyst composition according to claim 1, wherein each of the monocoordinated phosphine ligand represented by Formula 1 and the monocoordinated phosphine ligand represented by Formula 2 is comprised in an amount of 0.5 to 80 moles based on one mole of a central metal of the transition metal catalyst represented by Formula 3.

5. The catalyst composition according to claim 1, wherein the monocoordinated phosphine ligand represented by Formula 1 is tri-o-tolylphosphine or tris(o-methoxyphenyl)phosphine.

6. The catalyst composition according to claim 1, wherein the monocoordinated phosphine ligand represented by Formula 2 is cyclopentyldiphenylphosphine or cyclohexyldiphenylphosphine.

7. The catalyst composition according to claim 1, wherein a content of the transition metal catalyst represented by Formula 3 is 1 to 1,000 ppm based on the catalyst composition.

8. The catalyst composition according to claim 1, wherein the transition metal catalyst represented by Formula 3 is one or more selected from the group consisting of cobalt carbonyl $[Co_2(CO)_8]$, acetylacetonato dicarbonyl rhodium $[Rh(AcAc)(CO)_2]$, rhodium acetylacetonato carbonyl triphenylphosphine $[Rh(AcAc)(CO)(TPP)]$, hydrido carbonyl tri(triphenylphosphine)rhodium $[HRh(CO)(TPP)_3]$, acetylacetonato dicarbonyl iridium $[Ir(AcAc)(CO)_2]$, and hydrido carbonyl tri(triphenylphosphine)iridium $[HIr(CO)(TPP)_3]$.

9. The catalyst composition according to claim 1, wherein the catalyst composition further comprises one or more solvents selected from the group consisting of propane aldehyde, butyraldehyde, pentyl aldehyde, valeraldehyde, acetone, methyl ethyl ketone, methyl isobutyl ketone, acetophenone, cyclohexanone, ethanol, pentanol, octanol, texanol, benzene, toluene, xylene, orthodichlorobenzene, tetrahydrofuran, dimethoxyethane, dioxane, methylene chloride, and heptane.

10. A method of hydroformylating an olefinic compound, the method comprising a step of preparing an aldehyde by reacting an olefinic compound with a synthetic gas of carbon monoxide and hydrogen $(CO/H_2)$ in a presence of the catalyst composition according to claim 1.

11. The method according to claim 10, wherein the olefinic compound is a compound represented by Formula 4 below:

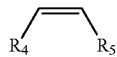

[Formula 4]

wherein $R_4$ and $R_5$ are each independently hydrogen, a $C_1$ to $C_{20}$ alkyl group, fluorine (—F), chlorine (—Cl), bromine (—Br), trifluoromethyl (—CF$_3$), or a $C_6$ to $C_{20}$ aryl group substituted with 0 to 5 substituents, and the aryl group is substituted with nitro (—NO$_2$), fluorine (—F), chlorine (—Cl), bromine (—Br), methyl, ethyl, propyl, or butyl.

12. The method according to claim 10, wherein the olefinic compound is one or more selected from the group consisting of ethene, propene, 1-butene, 1-pentene, 1-hexene, 1-octene and styrene.

13. The method according to claim 10, wherein a selection ratio of normal aldehyde to iso aldehyde in the prepared aldehyde is 2.5 or less.

14. The method according to claim 10, wherein a mix ratio in moles of carbon monoxide:hydrogen in the synthetic gas (CO/H$_2$) is 5:95 to 70:30.

* * * * *